US006768800B2

(12) United States Patent
Enamito et al.

(10) Patent No.: US 6,768,800 B2
(45) Date of Patent: Jul. 27, 2004

(54) ACTIVE NOISE CONTROLLER AND CONTROLLING METHOD

(75) Inventors: Akihiko Enamito, Kawasaki (JP); Hajime Kudo, Chiba (JP); Yoshiyuki Sato, Inagi (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 344 days.

(21) Appl. No.: 09/941,685

(22) Filed: Aug. 30, 2001

(65) Prior Publication Data

US 2002/0041690 A1 Apr. 11, 2002

(30) Foreign Application Priority Data

Aug. 31, 2000 (JP) ...................................... 2000-262483

(51) Int. Cl.[7] ................................................ A61F 11/06
(52) U.S. Cl. ................................................... 381/71.5
(58) Field of Search .............................. 381/71.1, 71.2, 381/71.3, 71.5

(56) References Cited

U.S. PATENT DOCUMENTS

| | | | | |
|---|---|---|---|---|
| 5,414,230 A | * | 5/1995 | Nieuwendijk et al. | 181/206 |
| 5,692,053 A | * | 11/1997 | Fuller et al. | 381/71.3 |
| 5,822,439 A | * | 10/1998 | Sakiyama et al. | 381/71.1 |
| 6,192,133 B1 | * | 2/2001 | Enamito et al. | 381/71.5 |

OTHER PUBLICATIONS

M. Nishimura, et al., J. Acoust. Soc., vol. 45, No. 9 pps. 672–680, "Active Control of Noise Radiated from Duct Output," 1989.

* cited by examiner

*Primary Examiner*—Minsun Oh Harvey
*Assistant Examiner*—Brian T. Pendleton
(74) *Attorney, Agent, or Firm*—Oblon, Spivak, McClelland, Maier & Neustadt, P.C.

(57) ABSTRACT

An active noise controller includes a duct (2) of a stainless steel having the shape of a pipe and provided with an opening (1) at a first end thereof, and a loudspeaker (3)connected to a second end of the duct (2). The duct (2) is disposed with its opening (1) located at a distance not greater than half the wavelength of a sound produced by a sound source (4) from the sound source (4) so as to face the sound source (4). A sound produced by the vibration of the vibrating member (5) of the loudspeaker (3) travels from the second end of the duct (2) through the duct (2) to the first end of the same, and the sound is radiated toward the sound source (4). The sound radiated through the opening (1) has a frequency substantially equal to that of an unnecessary sound included in the sound produced by the sound source (4), an amplitude substantially equal to that of the unnecessary sound and a phase substantially opposite to that of the unnecessary sound. The acoustic power of the unnecessary sound can be reduced by the sound produced by the loudspeaker (3), propagated through the duct (2) and radiated toward the sound source (4). The active noise controller is capable of achieving three-dimensional sound suppression with out being affected by heat and vibrations.

18 Claims, 5 Drawing Sheets

ACTIVE NOISE CONTROLLER AND CONTROLLING METHOD

BACKGROUND OF THE INVENTION

1. Field of the Invention

The present invention relates to an active noise controller and controlling method and, more particularly, to a three-dimensional active noise controller incorporated into a power generating system for private power generation or a transformer.

2. Description of the Related Art

Frequencies of audible sounds are in the range of 20 Hz to 20 kHz. Unwanted sounds unpleasant to human, among audible sounds, are called noises. There are various methods of controlling noises. For example, an active noise controller for controlling noise unidirectionally propagating through an exhaust duct uses an additional-sound-producing loudspeaker placed in the exhaust duct as an additional sound source. This active noise controller is called a one-dimensional active noise controller and has been prevalently used. The unidirectional active noise controller controls only sounds propagating past a position where the loudspeaker is placed.

The one-dimensional active noise controller is intended for suppressing only noises propagating through an exhaust duct, i.e., one-dimensional sounds, and is not intended for suppressing noises emitted by a sound source placed in an open space and three-dimensionally propagating in the open space. The one-dimensional active noise controller is capable of suppressing only part of sounds propagating through the exhaust duct and is incapable of suppressing sounds produced in other part of the exhaust duct.

Theoretically, the sound suppressing effect of a three-dimensional active noise controller intended for suppressing three-dimensionally propagating sounds can be enhanced by disposing the additional-sound-producing loudspeaker for producing an additional sound close to a noise source. Noise suppressing effect can be realized even at a position remote from the noise source. However, it is difficult to dispose the additional-sound-producing loudspeaker close to the noise source because the additional-sound-producing loudspeaker is affected by heat and vibrations generated by a device as a noise source or by a device disposed near the noise source. Since there is a technical trend of miniaturizing a system including the device as a noise source, it is difficult to secure a space available for installing the additional-sound-producing loudspeaker in the system including the device as a noise source, and hence the three-dimensional active noise controller is unable to suppress noises satisfactorily.

SUMMARY OF THE INVENTION

The present invention has been made in view of the foregoing problems in the conventional noise control apparatus and it is therefore an object of the present invention to provide an active noise controller capable of exercising a satisfactory noise suppressing effect without being affected by heat and vibrations generated by a noise source or a device disposed near a noise source.

According to the present invention, an active noise controller includes: an additional sound source that produces a sound of a frequency substantially equal to that of an unnecessary sound among sounds emitted by an unnecessary sound source to reduce the acoustic power of at least the unnecessary sound, and a duct connected to the additional sound source to conduct a sound produced by the additional sound source; wherein the duct has an opening through which the sound emitted by the additional sound source is radiated, and the duct is formed such that the sound emitted by the additional sound source and having a phase substantially opposite to that of the unnecessary sound is radiated through the opening into the vicinity of the unnecessary sound producing source to cancel out and reduce acoustic power of the unnecessary sound when the opening is at a distance not greater than about half the wavelength of the unnecessary sound from the unnecessary sound producing source.

A transformer provided with the active noise controller of the present invention includes a core, coils wound on the core, a tank holding the core and the coil therein, the additional sound source capable of producing a sound of a frequency substantially equal to that of a sound to be controlled to reduce the acoustic power of the sound among those produced by the core and the coils, and disposed apart from the tank, and the duct connected to the additional sound source to conduct the sound produced by the additional sound source to the tank and to send out the sound produced by the additional sound source to the vicinity of the tank. The distance between the tank and the opening is not greater than substantially half the wavelength of the unnecessary sound to be controlled. The phase of the sound sent out through the opening is opposite to that of the unnecessary sound to be controlled.

A power generating system provided with the active noise controller of the present invention includes a power generator, an internal combustion engine (hereinafter referred to simply as "engine"), the additional sound source capable of producing a sound of a frequency substantially equal to that of a sound to be controlled to reduce the acoustic power of the sound among those produced by the engine, and disposed apart from the engine, and the duct connected to the additional sound source to conduct the sound produced by the additional sound source to the engine and to send out the sound produced by the additional sound source to the vicinity of the engine. The distance between the engine and the opening is not greater than substantially half the wavelength of the unnecessary sound to be controlled. Pistons that move in cylinders formed in the engine produce sounds. The phase of the sound sent out through the opening is opposite to that of the unnecessary sound to be controlled.

Acoustic power expressed in watt is the amount of energy produced in a unit time by a sound source. Acoustic power level (dB) is represented by $10 \log (I/I_0)$, where $I_0=10^{-12}$ (w) is reference acoustic power; that is, acoustic power is a specific energy value representing the magnitude of noise. Sound pressure level (dB) is the pressure variation P ($N/m^2$) of a sound wave at an observation point expressed by $20 \log (P/P_0)$ (dB), where $P_0$ is reference sound pressure expressed by $P_0=2\times10^{-5}$ ($N/m^2$).

For example, when the acoustic power level of a sound source is 80 dB, the sound pressure level at a position around the sound source is dependent on the distance between the sound source and the position; for example, the sound pressure level at one position is 70 dB and that at another position is 60 dB. If the acoustic power level of the sound source is reduced, the sound pressure levels at positions decreases accordingly.

BRIEF DESCRIPTION OF THE DRAWINGS

The above and other objects, features and advantages of the present invention will become more apparent from the following description taken in connection with the accompanying drawings, in which.

DESCRIPTION OF THE PREFERRED EMBODIMENTS

Figure 1:
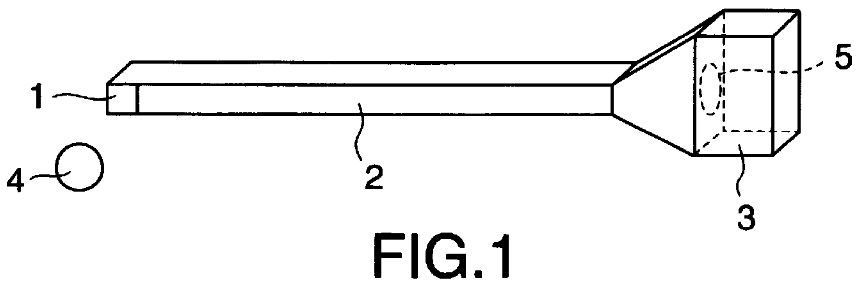
FIG. 1 is a perspective view of an active noise controller in a first embodiment according to the present invention.

First Embodiment (FIG. 1)

An active noise controller in a first embodiment according to the present invention shown in FIG. 1 is used when the frequency spectrum of sounds produced by a sound source, i.e., an unnecessary sound producing source, is known beforehand. The frequency spectrum of the sounds produced by the sound source may be determined by calculation on the basis of the physical characteristics of the sound source and the mechanical characteristics of a device including the sound source or by measuring the sounds produced by the sound source when the device including the sound source is operated temporarily by a microphone.

A noise, i.e., a sound to be controlled or suppressed, is a sound of a low frequency in the range of several tens to several hundreds hertz having the highest sound pressure level among those produced by the sound source.

The active noise controller includes a duct 2 of a stainless steel having the shape of a hollow pipe and provided with an opening 1 at a first end thereof, and a loudspeaker 3 (additional sound source)connected to a second end of the duct 2. The duct 2 is disposed with its opening 1 located at a predetermined distance from a sound source 4 so as to face the sound source 4. Although it is preferable that the opening 1 is disposed at the shortest possible distance from the sound source 4, the distance is not greater than half the wavelength λ of the noise produced by the sound source 4 for effective noise control. The vibrating member of the loudspeaker 3 is set in parallel to a cross section of the duct 2. A sound produced by the vibration of the vibrating member 5 of the loudspeaker 3 travels from the second end of the duct 2 through the duct 2 to the first end of the same, and the sound is radiated toward the sound source 4. The sound radiated through the opening 1 has a frequency substantially equal to that of an unnecessary sound included in the sound produced by the sound source 4, an amplitude substantially equal to that of the unnecessary sound and a phase substantially opposite to that of the unnecessary sound. The acoustic power of the unnecessary sound included in the sound produced by the sound source 4 can be reduced by the sound produced by the loudspeaker 3, propagated through the duct 2 and radiated toward the sound source 4.

Acoustic power reduction η when one point sound source and one additional sound source are in an open space is expressed by Expression (1)

$$\eta = 10\log\left\{1-\left(\frac{\sin kd}{kd}\right)^2\right\}\ (\text{dB}) \tag{1}$$

where k=2πf/c, d is the distance between the sound source and the additional sound source, f is the frequency (Hz) of the noise produced by the sound source and c is sonic speed (m/s).

As obvious from Expression (1), the shorter the distance d between the sound source 4 and the additional sound source 3, the greater is acoustic power reduction and the higher the sound suppressing effect, provided that the frequency f is fixed; that is, the closer the opening 1 to the sound source 4, the greater is the reduction of the acoustic power of the noise produced by the sound source 4.

Thus, as obvious from Expression (1), the closer the additional sound source 3 to the sound source 4, the greater is the effect of the active noise controller in the first embodiment on suppressing the noise of the frequency to be controlled. However, most practical apparatus do not have sufficient space available for installing a loudspeaker and the disposition of a loudspeaker near the sound source is subject to restrictions relating to heat and vibration or appearance. Thus it is difficult to dispose a large loudspeaker that regenerates sounds of low frequencies near the sound source. The duct 2 of the active noise controller in the first embodiment can be installed in the power generating system without requiring a large space with the opening 1 of the duct 2 disposed near the sound source 4. Consequently, the active noise controller is able to exercise a high noise suppressing effect. The sound of the specific frequency emitted by the sound source 4, i.e., acoustic power corresponding to the spatial average of a sound spreading in a space, can be reduced and, consequently, the sound spreading in all directions from the sound source can be controlled. Although acoustic power cannot be locally reduced to zero, the noise suppressing effect is available even if the intensity of the sound is enhanced by the interference between the noise emitted by the sound source 4 and the sound radiated through the opening 1 to reduce the acoustic power of the sound emitted by the sound source 4 because the acoustic power is small. If the distance between the sound source 4 and the opening 1 is greater than half the wavelength of the noise, the acoustic power of the sound produced by the loudspeaker 3 exceeds that of the noise produced by the sound source 4 and hence the noise suppressing effect is unavailable.

When the sound emitted by the sound source 4 is a periodic sound having a substantially fixed frequency, the noise suppressing effect of the active noise controller is particularly satisfactory.

Second Embodiment

An active noise controller in a second embodiment according to the present invention will be described with reference to FIG. 2, in which parts like or corresponding to those of the active noise controller in the first embodiment are denoted by the same reference characters and the description thereof will be omitted to avoid duplication.

The active noise controller in the second embodiment includes a duct 2 having a length determined so that the duct 2 resonates with a sound of a particular frequency. The length of the duct 2 is determined so that the resonance frequency of the duct 2 is equal to the frequency of a sound to be controlled among sounds produced by a sound source 4. A resonance sound produced by the resonation of the duct 2 is radiated through an opening 1 toward the sound source 4. Thus, input power to a loudspeaker 3 may be small. The duct 2 is able to conduct the sound efficiently to the opening 1. Since the input power to the loudspeaker 3 may be small, the life of the loudspeaker 3 is extended.

Figure 2:
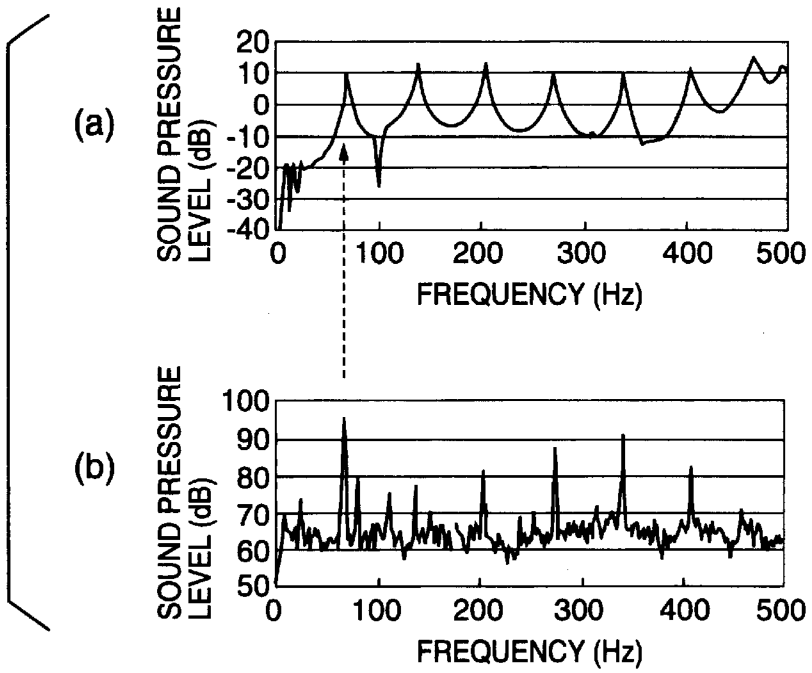
FIG. 2 is a perspective view of an active noise controller in a second embodiment according to the present invention.

FIG. 2(*a*) is a graph showing measured sound pressure levels of sounds of different frequencies at the opening 1 of the duct 2 and FIG. 2(*b*) is a graph showing the relation between sound pressure level and frequency of a sound produced by the sound source. As shown in FIG. 2(*b*) the sound has a peak at 70 Hz. The duct 2 is designed so as to resonate with a sound of a frequency substantially equal to 70 Hz as indicated by the arrow in FIG. 2(*a*).

The resonant sound is radiated through the opening 1 toward the sound source 4 to suppress the noise. Since the sound pressure level of a sound produced by a vibrating member 5 is enhanced by resonance in the duct 2 and the sound has an enhanced sound pressure, the loudspeaker 3 does not need a large input, load on the loudspeaker 3 is small, the power consumption of the loudspeaker 3 is low and the loudspeaker 3 has a long life.

Third Embodiment

Figure 3:
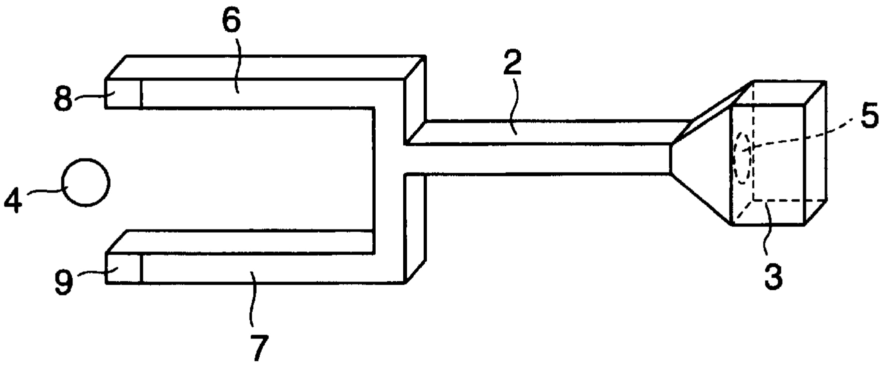
FIG. 3 is a perspective view of an active noise controller in a third embodiment according to the present invention.

An active noise controller in a third embodiment according to the present invention will be described with reference to FIG. 3. A duct 2 provided with a single loudspeaker 3 and having branch ducts and a plurality of openings features the active noise controller in the third embodiment. Referring to FIG. 3, the duct 2 extended between a vibrating member 5 and a sound source 4 has two branch ducts 6 and 7 provided, respectively, with openings 8 and 9 through which sound is radiated toward the sound source 4. The openings 8 and 9 are located opposite to the sound source 4 in point-symmetrical relation with respect to the sound source 4. Distances between the openings 8 and 9, and the sound source 4 are not greater than half the wavelength of the sound produced by the sound source 4. The duct 2 may have three or more branch ducts. Distances between a branching point where the duct 2 is branched and the openings 8 and 9 need not necessarily be equal.

The noise control effect of the active noise controller in the third embodiment will be described with reference to FIGS. 4 and 5. In FIG. 5, the distance between the sound source 4 and an additional sound source was 10 cm and measurement was performed at an ordinary temperature.

Figure 4:
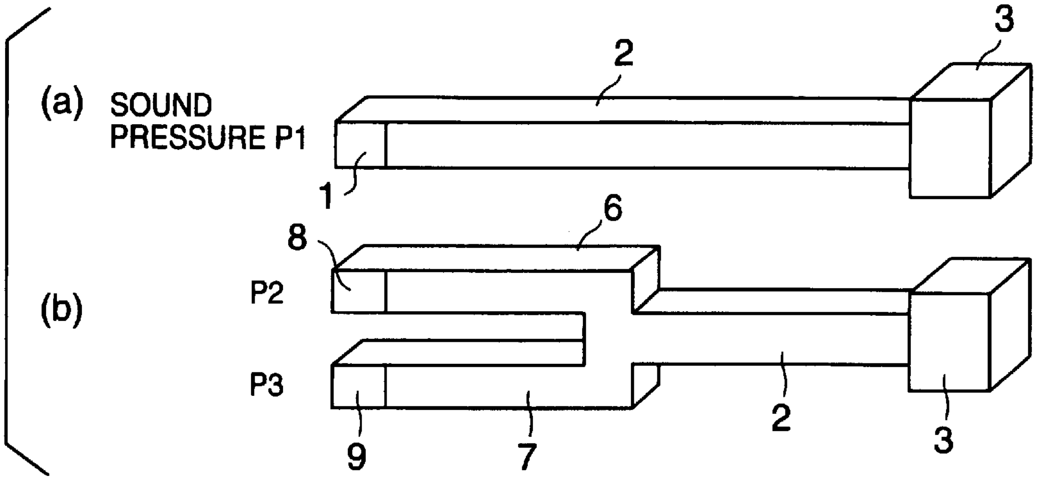
FIGS. 4(*a*) and 4(*b*) are perspective views of assistance in explaining the operation of the active noise controller in the third embodiment.
Figure 5:
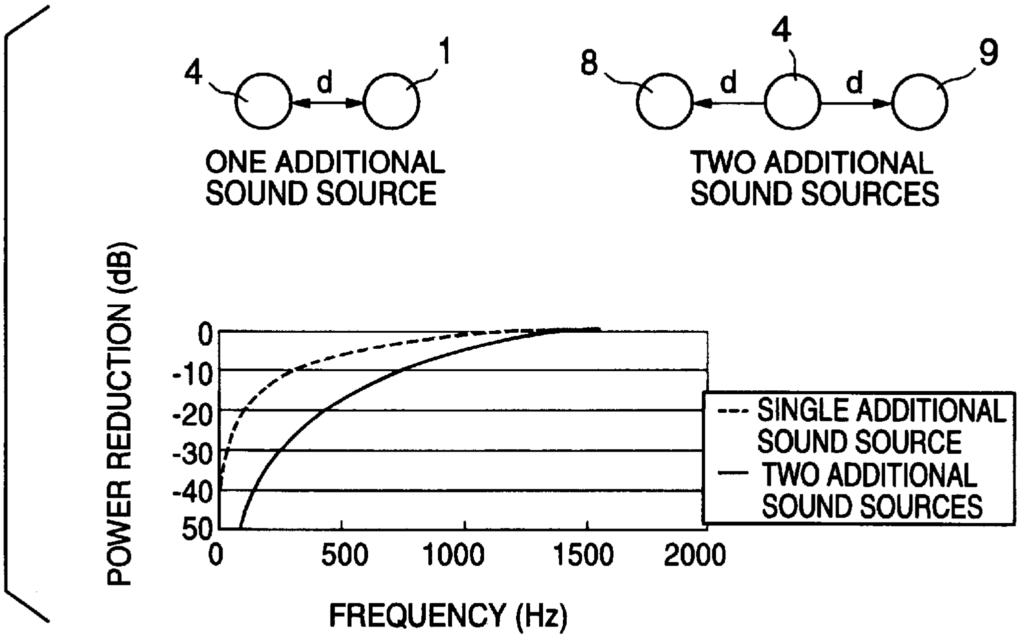
FIG. 5 is a view of assistance in explaining the operation of the active noise controller in the third embodiment.

When the lengths of the branch ducts 6 and 7 between the branching point and the openings 8 and 9 are equal as shown in FIG. 4(*b*), sound pressures P2 and P3 of sounds radiated through the openings 8 and 9, respectively, are equal, which is equivalent to the placement of two additional sound sources that emit sounds of the same amplitude and the same phase in an open space. The sound pressures P2 and P3 are lower than a sound pressure P1 at an opening 1 in FIG. 4(*a*).

Acoustic power reduction $\eta$ when the duct 2 has the two branch ducts 6 and 7 can be expressed by Expression (2)

$$\eta = 10\log\left\{1 - \frac{2\left(\frac{\sin kd}{kd}\right)^2}{1 + \frac{\sin kL}{kL}}\right\}(\text{dB}) \qquad (2)$$

where d is the distance between the sound source and the additional sound source and L is the distance between the additional sound sources.

It is know from FIG. 5 that the reduction of the acoustic power of the sound produced by the sound source 4 when the active noise controller is provided with the two openings 8 and 9 is greater than that when the active noise controller is provided with a single opening 1. The frequency of a sound that causes a acoustic power reduction of 3 dB was about 1100 Hz when the active noise controller was provided with two additional sound sources. The frequency of a sound that causes a acoustic power reduction of 3 dB was about 750 Hz when the active noise controller was provided with a single additional sound source.

As obvious from the foregoing description, the active noise controller in the third embodiment is provided with the single loudspeaker 3 and is capable of exercising an enhanced noise suppressing effect by disposing the duct 2 so that the openings of the branch ducts are located near the sound source. It is most desirable to locate the plurality of openings point-symmetrically with respect to the sound source 4. When the plurality of openings are arranged at equal intervals so as to surround the sound source 4, sound suppressing effect is uniform regardless of position relative to the sound source 4 and sound control can be effectively achieved.

Fourth Embodiment

An active noise controller in a fourth embodiment according to the present invention will be described with reference to FIG. 6. The active noise controller in the fourth embodiment is featured by a duct 2 having branch ducts 10 and 11 respectively having different lengths, i.e., distances between a branching point and openings 12 and 13 formed in the branch ducts 11 and 12, respectively. The duct 2 is disposed so that the openings are located near two different sound sources 4, respectively.

Figure 6:
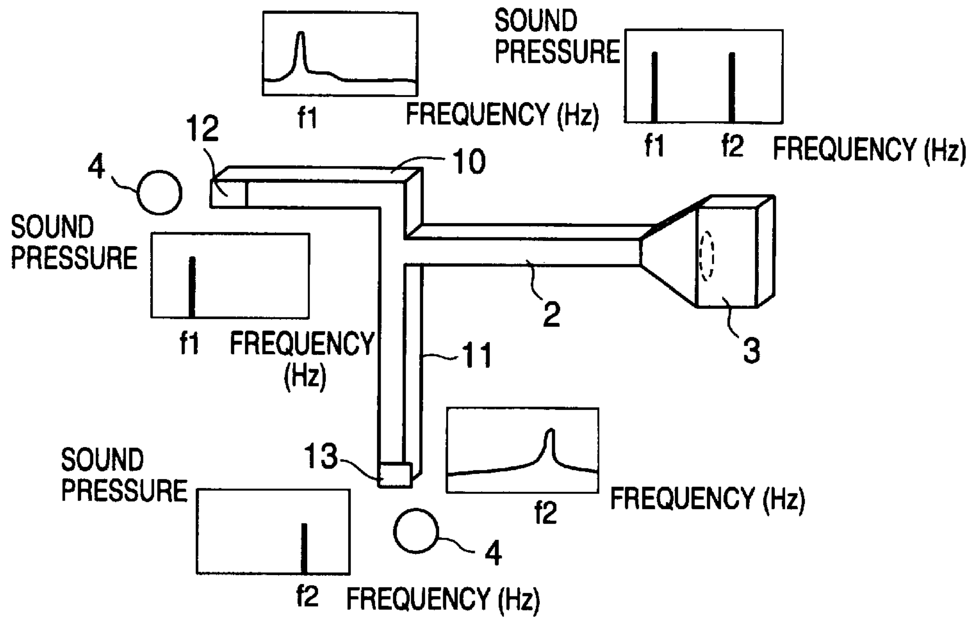
FIG. 6 is a perspective view of an active noise controller in a fourth embodiment according to the present invention.

Referring to FIG. 6, the duct 2 branches off at a branching point into the two branch ducts 10 and 11. The opening 12 formed at the free end of the branch duct 10 is located near the sound source 4, and the opening 13 formed at the free end of the branch duct 11 is located near the other sound source 4. The branch ducts 10 and 11 have different lengths, respectively. The distances between the openings 12 and 13, and the sound sources 4 are not greater than half the wavelengths of sounds produced by the corresponding sound sources 4, respectively. The distances between a vibrating member 5 and the openings 12 and 13 are dependent on the resonance frequencies of the branch ducts 12 and 13. The duct 2 may have three or more branch ducts.

A loudspeaker 3 produces a complex sound including a sound of an f1 Hz and a sound of f2 Hz. The lengths of the branch ducts 10 and 11 are determined so that the branch ducts 10 and 11 resonate to sounds of f1 and f2 Hz, respectively. For example, the amplified sound of f1 Hz and the amplified sound of f2 Hz are radiated through the openings 12 and 13 toward the sound sources 4, respectively. The sounds of the different frequencies f1 and f2 does not interfere with each other in a section of the duct 2 between the vibrating member 5 and the branching point. The sounds of the different frequencies f1 and f2 Hz are separated at the branching point and hence the branching point serves as an acoustic filter.

Thus the active noise controller in the fourth embodiment is capable of substantially simultaneously suppressing the noises of specific frequencies produced by the plurality of sound sources 4 that produces sounds of different frequencies by using the single loudspeaker 3. The active noise controller is applicable to noise suppression in a place where a plurality of loudspeaker cannot be installed, can be installed in a small space at small expenses.

Fifth Embodiment

An active noise controller in a fifth embodiment according to the present invention will be described with reference to FIG. 7. The active noise controller in the firth embodiment is featured by a duct 2 provided with an opening 1 in a part between the opposite ends thereof.

Figure 7:
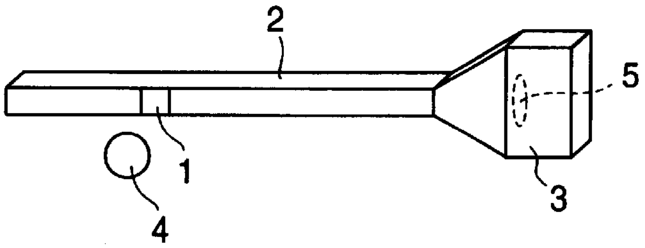
FIG. 7 is a perspective view of an active noise controller in a fifth embodiment according to the present invention.

Referring to FIG. 7, the opening 1 is formed in a part of the duct other than the free end of the duct 2. The free end of the duct is a close end not connected to a loudspeaker 3. The duct 2 is disposed with the opening 1 located opposite to a sound source 4. The position of the opening 1 is determined so that the duct 2 is able to resonate with a sound of a specific frequency. The operation of the active noise controller in the fifth embodiment is the same as that of the active noise controller in the first embodiment.

The active noise controller in the fifth embodiment is used when the duct 2 cannot be disposed with the free end located near the sound source 4. Since the position of the opening 1 can be properly determined after fabricating the duct 2 so that the opening 1 corresponds to the sound source 4. Thus, the active noise controller in the fifth embodiment has an increased degree of freedom of design and the opening 1 can be formed in a desired part of the duct 2. The opening 1 can be formed in a part of the duct at a distance not greater than half the wavelength of the sound produced by the sound source 4 so that the duct 2 is able to resonate. When any position that enables the duct 2 to resonate cannot be found, the opening 1 may be formed in a part the nearest to the sound source 4 of the duct 2.

Sixth Embodiment

An active noise controller in a sixth embodiment according to the present invention will be described with reference to FIG. 8. Microphones 15 disposed near an opening 1 formed in a duct 2 feature the active noise controller in the sixth embodiment.

The active noise controllers in the first to the fifth embodiment are used to suppress a noise of a known specific frequency included in the sound having a known frequency spectrum produced by the sound source. The active noise controller in the sixth embodiment is used for suppressing a noise of a specific frequency included in a sound having an unknown frequency spectrum produced by a sound source.

Figure 8:
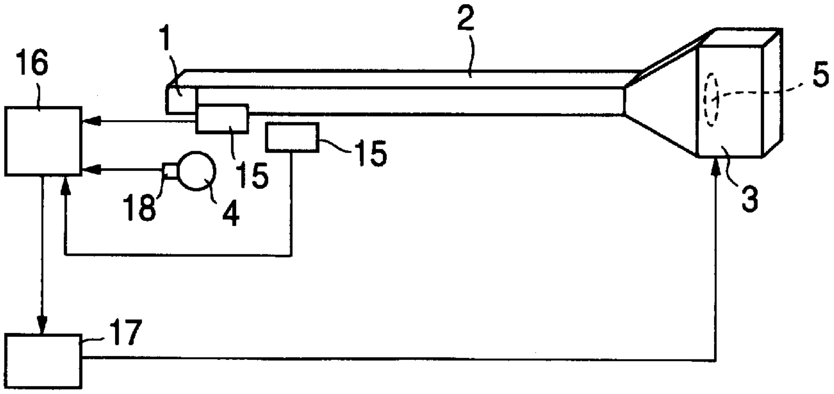
FIG. 8 is a perspective view of an active noise controller in a sixth embodiment according to the present invention.

Referring to FIG. 8, the two microphones 15 are disposed near the opening 1 of the duct 2. The microphones 15 are connected to a controller 16. The controller 16 is connected to a driver 17 for applying voltage to a loudspeaker 3. The microphones 15 serve as sound pressure measuring devices and may be electrodynamic microphones, electrostatic microphones or piezoelectric microphones. An accelerometer 18 is disposed in contact with or near the sound source 4. The acceleration sensor 18 gives a signal to the controller 16.

In operation, the microphones 15 measure the sound pressure of a sound radiated through the opening 1, and give electric signals representing measured sound pressures to the controller 16. The accelerometer 18 measures the acceleration of the sound source 4 and gives a signal representing a measured acceleration to the controller 16. The controller 16 obtains the frequency spectrum of the sound produced by the sound source 4 from the acceleration of the sound source 4 measured by the accelerometer 18 and extracts a sound of a low frequency in the range of several tens to several hundreds hertz and having the highest sound pressure level. The controller 16 differentiates two measured sound pressures with respect to the distance between the microphones 15 to obtain a particle velocity, and calculates a acoustic power for reducing the acoustic power of the sound of the extracted frequency on the basis of the measured sound pressures, the calculated particle velocity and the area of the opening 1. The controller 16 produces a drive signal corresponding to the calculated acoustic power, for operating the driver 17. The distance between the microphones 15 and the area of the opening 1 are known values previously stored in a storage device included in the controller 16. A acoustic power control signal produced by the controller 16 is given to the driver 17. Then, the driver 17 drives the loudspeaker 3 according to the acoustic power control signal and the loudspeaker 3 operates according to the acoustic power control signal to generates a sound. The foregoing operations are performed successively. The controller 16 controls the loudspeaker 3 in an adaptive control mode to vary the components of the sound generated by the loudspeaker 3 according to the sound emitted by the sound source 4 and measured by the microphones 15.

The controller 16 of the active noise controller in the sixth embodiment calculates the acoustic power of the sound emitted by the sound source 4 on the basis of measured data provided by the microphones 15 and controls the loudspeaker 3 on the basis of the calculated acoustic power in a feed-forward control mode. Thus the noise suppressing effect of the active noise controller can be improved by adaptive control so that the loud speaker 3 produces an optimum sound for noise suppression. Thus the characteristic of the sound produced by the sound source 4 does not need to be measured beforehand by operating a system including the sound source 4. Sounds of different frequencies can be suppressed by measuring the sound pressure of the sound emitted by the sound source 4 by the microphones 15 and determining the characteristic of the sound to be produced by the loudspeaker 3 on the basis of the measured data. The active noise controller in the sixth embodiment is effective in suppressing noise when the sound source 4 produces a sound of variable frequency or when the frequency of a sound to be suppressed is changed frequently.

An active noise controller in a seventh embodiment according to the present invention will be described with reference to FIG. 9. An opening 1 having an area S1 smaller than the area S2 of a vibrating member 5 features the active noise controller in the seventh embodiment.

Figure 9:
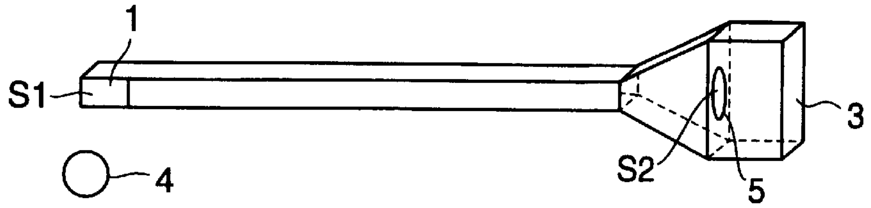
FIG. 9 is a perspective view of an active noise controller in a seventh embodiment according to the present invention.

Referring to FIG. 9, the area S1 of the opening 1 is smaller than the area S2 of the vibrating member 5. The sectional area of a part of a duct 2 between the vibrating member 5 and the opening 1 may be either greater or smaller than the area of the vibrating member 5 or the opening 1.

When the duct 2 is thus formed, the particle velocity of a sound radiated through the opening 1 is higher than the particle velocity on the vibrating member 5, so that the entry of foreign matters into the duct can be prevented. If foreign matters exist the duct 2, the foreign matters prevents the duct 2 from resonating with a desired frequency or cause the energy of a sound propagating through the duct to decrease, which reduces the noise suppressing effect of the duct 2. The active noise controller in the seventh embodiment is free from such problems.

An active noise controller in an eighth embodiment according to the present invention will be described with reference to FIG. 10. A duct 2 provided with four openings 1 arranged around a sound source 4 features the active noise controller in the eighth embodiment.

Figure 10:
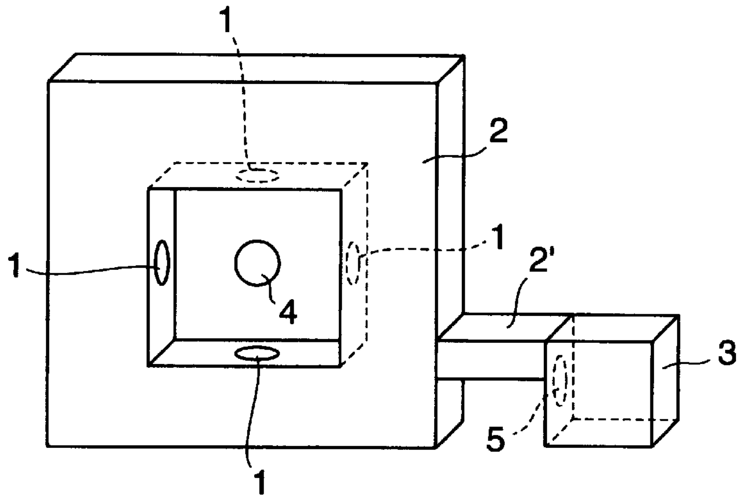
FIG. 10 is a perspective view of an active noise controller in an eighth embodiment according to the present invention.

Referring to FIG. 10, the duct 2 is formed in a shape substantially resembling a rectangular solid provided with a central rectangular through hole and is disposed so as to surround the sound source 4. The four inner side walls of the duct 2 are provided with the openings 1, respectively. A connecting duct 2' connects the duct 2 to a loudspeaker 3. A sound produced by the loudspeaker 3 propagates through the duct 2' and travels through the openings 1 arranged around the sound source 4 toward the sound source 4.

The duct 2 surrounding the sound source 4 suppresses noise produced by the sound source 4 efficiently and the screening function of the duct 2 further enhances the noise suppressing effect of the active noise controller.

The active noise controller in the eighth embodiment is particularly effective when applied to a double-glazed window for a movable structure, such as an aircraft or a passenger coach of a rapid train, or a building, such as a school building, a library building or a hospital building. In such an application, the window pane of the double-glazed window exposed to external noises is a sound source. The duct 2 provided with the plurality of openings 1, the connecting duct 2' and the loudspeaker 3 are arranged around a sash holding the outer and inner panes of the double-glazed window so as to cancel out sounds transmitted by the panes and propagating through a space between the two panes. Thus sounds propagating from outside the moving structure or the building into the movable structure or the building are suppressed, and a pleasant space isolated from unnecessary external noises can be provided for persons in the movable structure or the building. When the active noise controller has a plurality of ducts each provided with a plurality of openings and the plurality of ducts are installed so as to surround a plurality of windows, a single loudspeaker may be connected to the plurality of ducts by branch ducts to save the cost.

Ninth Embodiment

An active noise controller in a ninth embodiment according to the present invention will be described with reference to FIG. 11. The active noise controller in the ninth embodiment is applied to a power generating system including a power generator and an internal combustion engine (hereinafter referred to simply as "engine") for driving the power generator. In this case, the engine is a sound source.

Figure 11:
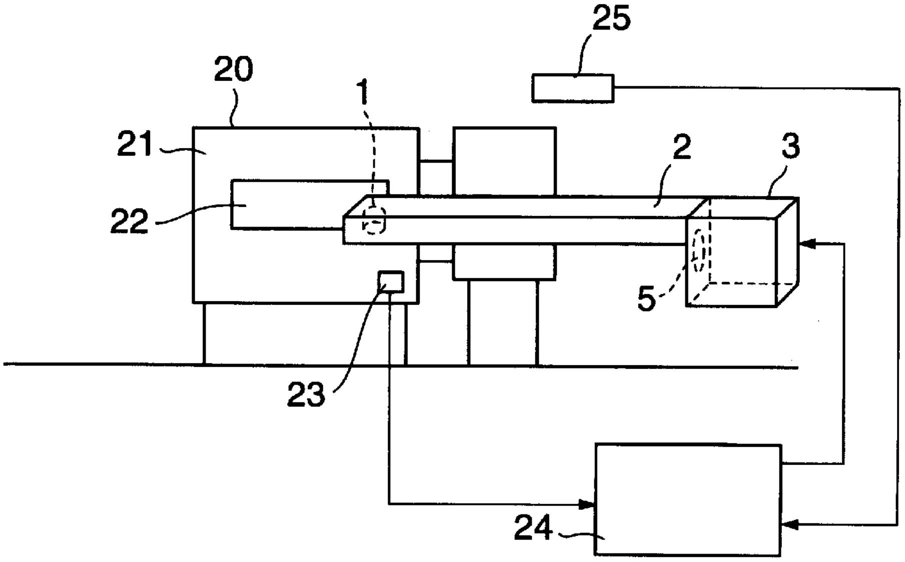
FIG. 11 is a perspective view of an active noise controller in a ninth embodiment according to the present invention.

As shown in FIG. 11, a power generating system 20 includes an engine 21 having a cylinder block 22, a vibration detector 23, a controller 24, a loud speaker 3, a duct 2 provided with an opening 1, and a microphone 25. Pistons, not shown, operate in cylinders formed in the cylinder block 22. The vibration detector 23 detects the vibration of the engine 21. The microphone 25 is disposed near the engine 21 so that the same may not be affected by heat and vibration. The vibration detector 23 and the microphone 25 are connected to the controller 24. The controller 24 is connected to the loudspeaker 3. The duct 2 is extended into the engine 21. An opening 1 formed in an inner end part of the duct 2 is located in the engine 21. The distance between the opening 1 and the piston is not greater than about half the wavelength of a sound generated by the piston.

The operation of the active noise controller in the ninth embodiment will be described. The piston reciprocating in the cylinder of the cylinder block 22 generates a vibration. Consequently, the engine 21 vibrates and produces a sound. The vibration detector 23 detects the vibration of the engine 21 generating the sound and sends a signal representing the vibration to the controller 24. The controller 24 gives a signal to make the loudspeaker 3 produce a sound that will interfere with the sound of the engine 21. The loudspeaker 3 produces a sound having a phase opposite to that of the sound produced by the engine 21 and an amplitude equal to that of the sound produced by the engine 21. The sound emitted by the loudspeaker 3 propagates through the duct 2 and is radiated through the opening 1 into the engine 21 to suppress the sound produced by the engine 21.

A sound pressure in the vicinity of the engine 21 measured by the microphone 25 is used to enhance the noise suppressing effect of the active noise controller. The microphone 25 sends a signal representing a measured sound pressure to the controller 25. Then the controller 25 generates a signal to make the loudspeaker 3 produce a sound capable of reducing the sound pressure measured by the microphone 25 to a minimum and gives the same to the loudspeaker 3. The loudspeaker 3 produce a sound represented by the signal, so that the sound pressure measured by the microphone 25 is reduced for noise suppression.

The active noise controller may be provided with a plurality of microphones 25 and a plurality of openings 1. The numbers and the positions of the microphones 25 and the openings 1 may be properly determined for the most effective noise suppression.

The active noise controller in the ninth embodiment is suitable for suppressing the noise generated by the engine of the power generating system. Thus the active noise controller makes the power generating system harmless to operators and the environment. The sound produced by the loudspeaker 3 is radiated through the opening 1 into the engine 21 for noise suppression. The microphone 25 measures sound pressure in the vicinity of the engine 21 and the loudspeaker 3 is controlled according to a measured sound pressure measured by the microphone 25 so as to produce a sound effective on the suppression of noise generated by the engine 21.

The active noise controller is applicable also to a movable structure provided with an engine, such as an automobile.

An active noise controller in a tenth embodiment according to the present invention will be described with reference to FIG. 12. The active noise controller in the ninth embodiment is applied to a transformer. In this case, an outer wall of a tank containing the transformer or an outer wall of a soundproof cover is a sound source.

Figure 12:
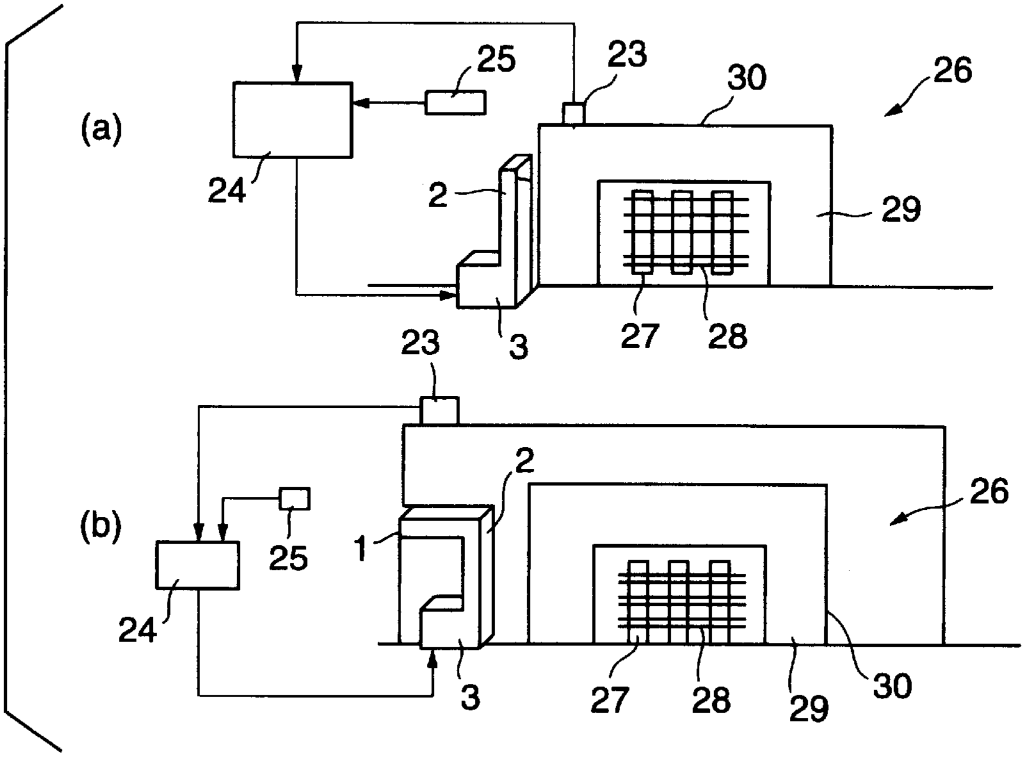
FIG. 12 is a perspective view of an active noise controller in a tenth embodiment according to the present invention.

Referring to FIG. 12(*a*), a transformer 26 has a core 27, coils 28, insulating oil 29 and a tank 30. The coils 28 are wound on the core 27. The coils 28 are immersed in the insulating oil 29 contained in the tank 30. A vibration detector 23 is attached to a side wall of the tank 30 to measure a vibration that propagates along the tank 30. The vibration detector 23 sends a signal representing a measured vibration to a controller 24. A microphone 25 is disposed near the tank 30. The microphone 25 sends a signal representing a measured sound to the controller 24. A duct 2 combined with a loudspeaker 3 and provided with an opening 1 is disposed such that a part provided with the opening 1 thereof is in close contact with a side wall of the tank 30. The distance between the tank 30 and the opening 1 of the duct 2 is not greater than half the wavelength of a sound generated by the vibrating tank 30. The controller 24 gives a control signal to the loudspeaker 3.

The vibration detector 23 measures the vibration of the wall of the tank 30 and sends a vibration signal representing a measured vibration to the controller 24. The controller 24 examines the vibration signal, determines components of a sound for suppressing the sound produced by the tank 30 and gives a control signal to make the loudspeaker 3 produce a sound that will suppress the sound produced by the tank 30 to the loudspeaker 3. The components of the sound are a phase opposite to that of the sound produced by the tank 30 and an amplitude equal to that of the sound produced by the tank 30.

The loudspeaker 3 generates a sound having a characteristic specified by the control signal. The sound generated by the loudspeaker 3 propagates through the duct 2 and is radiated through the opening 1 toward the side wall pf the tank 30. The controller 24 monitors the signal provided by the microphone 25, produces a control signal according to the signal provided by the microphone 25 and gives a control signal for reducing the sound pressure measured by the microphone to a minimum to the loudspeaker 3.

FIG. 12(*b*) shows another transformer 26 provided with the active noise controller. A soundproof cover 31 of concrete covers the transformer 26 to isolate the transformer 26 from the exterior of the transformer 26. A loudspeaker 3 and a duct 2 provided with an opening are disposed in a space between the soundproof cover 31 and the transformer 26. A part provided with the opening 1 of the duct 2 is substantially in close contact with the inner surface of the soundproof cover 31. The distance between the soundproof cover 31 and the opening 1 of the duct 2 is not greater than half the wavelength of a sound generated by the vibrating soundproof cover 31. A vibration detector 23, a microphone 25 and a controller 24, similarly to those shown in FIG. 12(*a*) are arranged on or near the wall of the soundproof cover 31, The noise suppressing effect of the active noise controller shown in FIG. 12(*b*) is similar to that of the active noise controller shown in FIG. 12(*a*).

The active noise controller in the tenth embodiment is suitable for suppressing the noise generated by the transformer 26. Thus the active noise controller makes the transformer 26 harmless to operators and the environment. The noise controller is capable of suppressing electromagnetic sounds of low frequencies generated by the electrostrictive vibration of the core 27 and difficult to suppress only by the soundproof cover. Since the soundproof cover can be simplified, the cost and weight can be reduced.

The present invention is not limited in its practical application to the foregoing embodiments and many changes and variations are possible without departing from the scope of the invention. For example, the duct may be provided with any suitable number of openings. The controller may be connected to the microphone by a radio communication system or a cable communication system, provided that the controller is able to receive the signal representing data measured by the microphone. When the active noise controller is provided with, for example, two ducts, it is most desirable that the ducts are point-symmetrical with respect to the sound source. When the active noise controller is provided with, for example, three ducts, it is most desirable that the ducts are arranged at angular intervals of 120° around the sound source. When the active noise controller is provided with, for example, four ducts, it is most desirable that the four ducts are arranged at angular intervals of 90° around the sound source. It is desirable to arrange a plurality of ducts (openings) at equal angular intervals around the sound source.

The active noise suppressor can be installed in equipment provided with a machine that performs a periodic operation, such as a motor, compressor or a cutting machine. Such equipment produces sound including a periodic sound as a principal component. The active noise controller is effective in suppressing such a periodic sound.

Although the invention has been described in its preferred embodiments with a certain degree of particularity, obviously many changes and variations are possible therein. It is therefore to be understood that the present invention may be practiced otherwise than as specifically described herein without departing from the scope and spirit thereof.

What is claimed is:

1. An active noise controller comprising:

an additional sound source that produces a sound of a frequency substantially equal to that of an unnecessary sound among sounds emitted by an unnecessary sound source to reduce the acoustic power of at least the unnecessary sound; and a duct connected to the additional sound source to conduct a sound produced by the additional sound source;

wherein the duct has an opening through which the sound emitted by the additional sound source is radiated, and the duct is formed such that the sound emitted by the additional sound source and having a phase substantially opposite to that of the unnecessary sound is radiated through the opening into the vicinity of the unnecessary sound source to cancel out and reduce acoustic power of the unnecessary sound when the opening is at a distance not greater than about half the wavelength of the unnecessary sound from the unnecessary sound source, and wherein a distance between the opening of the duct and the additional sound source is determined so that the duct resonates with the sound emitted by the additional sound source and having a frequency substantially equal to that of the unnecessary sound.

2. The active noise controller according to claim 1, wherein the duct is branched into a plurality of branch ducts, the plurality of branch ducts are provided with openings, respectively, and a sound of a phase opposite to that of the unnecessary sound is radiated through the openings into the vicinity of the unnecessary sound source.

3. The active noise controller according to claim 2, wherein the plurality of branch ducts comprise first and second branch ducts, a distance between the additional sound source and the opening of the first branch duct and a distance between the additional sound source and the opening of the second branch duct are substantially equal, respective resonance frequencies of the first and the second branch duct are substantially equal, sounds respectively having substantially equal frequencies are radiated through the respective openings of the first and the second branch duct toward the unnecessary sound source.

4. The active noise controller according to claim 3, wherein the respective openings of the plurality of branch ducts are arranged around the unnecessary sound source.

5. The active noise controller according to claim 2, wherein the plurality of branch ducts comprises first and second branch ducts, a distance between the additional sound source and the opening of the first branch duct and a distance between the additional sound source and the opening of the second branch duct are different, respective resonance frequencies of the first and the second branch duct are different, and sounds respectively having different frequencies are radiated through the respective openings of the first and the second branch duct toward the unnecessary sound source.

6. The active noise controller according to claim 5, wherein the sound emitted by the unnecessary sound source includes a plurality of unnecessary sounds of different frequencies to be suppressed, the frequencies of the sounds radiated through the openings of the first and the second branch duct, respectively, are substantially equal to those of the unnecessary sounds, respectively.

7. The active noise controller according to claim 6, wherein unnecessary sounds are produced by a plurality of unnecessary sound sources at different positions, the frequencies of the sounds radiated through the openings of the first and the second branch duct are substantially equal to those of the unnecessary sounds produced by the plurality of unnecessary sound sources, respectively, and the openings of the first and the second branch duct can be located at distances not greater than about half the wavelengths of the unnecessary sounds produced by the plurality of unnecessary sound sources, respectively.

8. The active noise controller according to claim 1, wherein the duct has the shape of a pipe, and the opening is formed in an end portion of the duct opposite to another end portion thereof connected to the additional sound source.

9. The active noise controller according to claim 1, wherein the duct has the shape of a pipe, and the opening is formed in a part of the duct at a distance from an end portion of the duct opposite to another end portion thereof connected to the additional sound source toward the unnecessary sound source.

10. The active noise controller according to claim 1 further comprising first and second sound pressure sensors for measuring sound pressure of the sound emitted by the additional sound source, spaced a distance apart from each other and disposed near the opening.

11. The active noise controller according to claim 10 further comprising:

a driving device configured to drive the additional sound source;

an accelerometer for measuring a frequency spectrum of the sound produced by the unnecessary sound source; and a control device that extracts a frequency of an unnecessary sound to be suppressed from the frequency spectrum obtained by the accelerometer, determines a particle velocity concerning sound by differentiating the sound pressures measured by the first and the second sound pressure sensor with respect to the distance between the first and the second sound pressure sensor, determines acoustic power necessary for suppressing the unnecessary sound on the basis of the frequency of the unnecessary sound extracted from the frequency spectrum, the particle velocity and data on an area of the opening, and controls the driving device on the basis of the determined acoustic power.

12. The active noise controller according to claim 1, wherein the additional sound source has a vibrating member capable of producing a sound, and the opening has an area smaller than an area of the vibrating member.

13. The active noise controller according to claim 1, wherein the duct has the shape of a ring having a plurality of openings therein, and the plurality of openings are formed in the duct so as to surround the unnecessary sound source and a sound of a phase opposite to that of the unnecessary sound is radiated through the openings into the vicinity of the unnecessary sound source.

14. The active noise controller according to claim 1, wherein the sound produced by the additional sound source has an amplitude substantially equal to that of the unnecessary sound to be suppressed among sounds produced by the unnecessary sound source.

15. The active noise controller according to claim 1, wherein a frequency of an unnecessary sound to be suppressed is extracted from a frequency spectrum of the sound produced by the unnecessary sound source, and the additional sound source produces a sound having a frequency substantially equal to that of the unnecessary sound to be suppressed.

16. The active noise controller according to claim 1, wherein the active noise controller is combined with a transformer, the transformer has a core, coils wound on the core, and a tank containing the core and the coil, and the unnecessary sound is produced by the core and the coil.

17. The active noise controller according to claim 1, wherein the active noise controller is combined with a power generating system including an internal combustion engine, and the internal combustion engine produces the unnecessary sound.

18. An active noise controlling method comprising:

preparing an additional sound source that produces a sound of a frequency substantially equal to that of an unnecessary sound among sounds emitted by an unnecessary sound source to reduce the acoustic power of at least the unnecessary sound;

setting an opening formed in a duct to be at a distance not greater than about half the wavelength of the unnecessary sound from the unnecessary sound producing source, the duct being connected to the additional sound source;

conducting a sound produced by the additional sound source within the duct; and emitting the sound through the opening into the vicinity of the unnecessary sound source to cancel out and reduce acoustic power of the unnecessary sound, wherein a distance between the opening of the duct and the additional sound source is determined so that the duct resonates with the sound emitted by the additional sound source and having a frequency substantially equal to that of the unnecessary sound.

* * * * *